United States Patent [19]

Imai et al.

[11] Patent Number: 4,902,677
[45] Date of Patent: Feb. 20, 1990

[54] TREATMENT OF HEART FAILURE OF MAMMALS WITH N⁶-SUBSTITUTED CYCLIC ADENOSINE MONOPHOSPHATES

[75] Inventors: Shoichi Imai, Kanagawa; Shigehiro Kataoka, Kashiwa; Junko Isono, Matsudo; Nobuyuki Yamaji; Motohiko Kato, both of Noda, all of Japan

[73] Assignee: Kikkoman Corporation, Noda, Japan

[21] Appl. No.: 159,747

[22] Filed: Feb. 24, 1988

[30] Foreign Application Priority Data

Feb. 25, 1987 [JP] Japan .................................. 62-40121

[51] Int. Cl.⁴ .............................................. A61K 31/70
[52] U.S. Cl. ........................................ 514/47; 514/48; 536/27; 536/28; 536/29
[58] Field of Search ........................ 536/24, 26, 27–29; 514/46, 47

[56] References Cited

U.S. PATENT DOCUMENTS 3,506,643  4/1970  Thiel et al. ............................. 536/26
3,856,776  12/1974  Cehovic et al. ........................ 536/27
3,915,958  10/1975  Shuman et al. ........................ 536/27
4,058,659  11/1977  Robins et al.

OTHER PUBLICATIONS

Meyer et al, "Synthesis and Biological Activity of Several 6–Substituted 9–β–D–Ribofuranosylpurine 3', 5'–Cyclic Phosphates," Biochemistry, vol. 11, No. 14, (1972), pp. 2704–2709.
Jon P. Miller et al, "Synthesis and Enzymatic and Inotropic Activity of Some New 8–Substituted and 6,8–Disubstituted Derivatives of Adenosine Cyclic 3', 5'–Monophosphate," J. Med. Chem. 1980 23, 242–251.
Lehninger, Biochemistry, Worth Publishers, New York, 1975, pp. 812–815.

Primary Examiner—Ronald W. Griffin
Assistant Examiner—L. Eric Crane
Attorney, Agent, or Firm—Banner, Birch, McKie and Beckett

[57] ABSTRACT

A composition for use in the treatment of heart failure of mammals which comprises, as its active ingredient, an N⁶-substututed-adenosine-3',5'-cyclic phosphate represented by the following general formula (I) or a physiologically acceptable salt thereof:

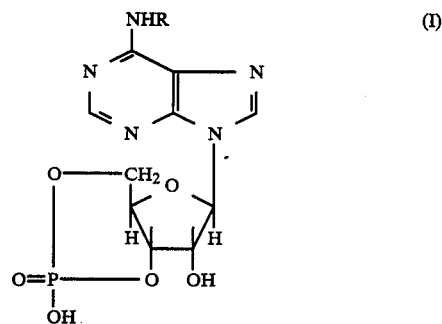

wherein R represents alkyl or aralkyl group and a pharmaceutically acceptable carrier, as well as a method for treating heart failure of mammals which comprises administering said composition.

9 Claims, No Drawings

TREATMENT OF HEART FAILURE OF MAMMALS WITH N⁶-SUBSTITUTED CYCLIC ADENOSINE MONOPHOSPHATES

BACKGROUND OF THE INVENTION

1. Field of the Invention

The present invention relates to a composition for use in the treatment of heart failure of mammals which comprises an $N^6$-substituted-adenosine-3',5'-cyclic phosphate or its physiologically acceptable salt as an active ingredient and a pharmaceutically acceptable carrier, as well as to a method for treating heart failure of mammals which comprises administering said composition.

2. Description of the Prior Art

Adenosine-3',5'-cyclic phosphate (hereinafter referred to as "C-AMP") itself exhibits no myocardial contractility when administered to heart [J. Pharmacol. Exptl. Therap., Vol. 139, 269 (1963)]. However, it is known that $N^6,2'$-O-dibutyryl C-AMP [Jpn. J. Pharmacol., 24, 499 (1974)] and 8-substituted-C-AMP [Chem. Pharm. Bull., 28, 1683 (1980)] which are derivatives of C-AMP have a myocardial contractile effect.

The present inventors conducted many studies on the pharmacological activities of various C-AMP derivatives to find that $N^6$-substituted-C-AMP and its salts have a strong positive inotropic effect and are useful as a therapeutic agent for heart failure of mammals. Based on this finding, the present invention was accomplished.

SUMMARY OF THE INVENTION

The present invention provides a composition for use in the treatment of heart failure of mammals which comprises, as its active ingredient, $N^6$-substituted-adenosine-3',5'-cyclic phosphate represented by the following general formula (I) or a physiologically acceptable salt thereof:

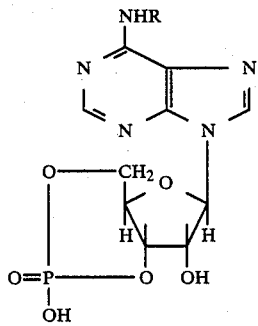

(I)

wherein R represents alkyl or aralkyl group and a pharmaceutically acceptable carrier, as well as a method for the treatment of heart failure of mammals which comprises administering said composition.

DETAILED DESCRIPTION OF THE INVENTION

Hereunder, the invention will be explained concretely.

The $N^6$-substituted-adenosine-3',5'-cyclic phosphate [the compound of formula (I)] or its physiologically acceptable salt used in the present invention as an agent for the treatment of heart failure of mammals may be synthesized by any methods. For example, it can be produced by reacting C-AMP with an aldehyde and then reducing the product as mentioned in Japanese patent application Kokai (Laid-Open) No. 60-239,496 (U.S. Appln. Ser. No. 727,062, now U.S. Pat. No. 4,751,293).

As group R in formula (I), the following groups are usually used: straight chain and branched chain alkyl groups having 2 to 14 carbon atoms such as ethyl, propyl, isopropyl, butyl, isobutyl, pentyl, isopentyl, hexyl, isohexyl, cyclohexyl, heptyl, isoheptyl, octyl, isooctyl, nonyl, isononyl, decyl, undecyl, dodecyl, tridecyl, tetradecyl and the like; and aralkyl groups such as furfuryl, benzyl, phenethyl, chlorobenzyl, hydroxybenzyl, methylbenzyl, methoxybenzyl groups and the like.

The above-mentioned compound (I) is put to use either in the form of free acid or in the form of a physiologically acceptable salt thereof. Examples of the physiologically acceptable salt include alkali metal salts such as potassium salt, sodium salt, and the like; ammonium salt; and organic ammonium salts such as triethyl ammonium salt, tributyl ammonium salt, and the like.

The composition of the present invention for use in the treatment of heart failure of mammals can be administered either orally or non-orally. The compound of formula (I), i.e. the active ingredient, is used in the form of a composition prepared by mixing it with appropriate pharmaceutically acceptable carriers.

The pharmaceutically acceptable carriers usable in the present invention include binders such as syrup, gum arabic, gelatin, sorbit, polyvinyl pyrrolidone, glycerine and the like; excipients such as lactose, sucrose, corn starch, crystalline cellulose, calcium phosphate, magnesium carbonate, mannitol, glycine, triglyceride and the like; lubricants such as magnesium stearate, talc, polyethylene glycol, silica and the like; disintegrators such as potato starch, sodium carboxymethylcellulose, potassium carboxymethylcellulose and the like; dispersants such as calcium metha-phosphate, sodium citrate, sodium alginate, surface active agents, and the like; wetting agents such as sodium lauryl sulfate and the like; and dissolving agents such as water, saline water, ethyl alcohol, polyethylene glycol, propylene glycol, dimethylsulfoxide, Krebs-Henselit solution (component: NaCl, 118 mM; KCl, 4.7 mM; $CaCl_2$, 2.5 mM; $NaHCO_3$, 2.5 mM; $MgSO_4$, 1.2 mM; $KH_2PO_4$, 1.2 mM; glucose 11 mM), etc. These carriers are used either alone or in the form of a mixture.

The composition forms adoptable in the present invention include solid compositions such as tablet, pill, powder, capsule, granule and the like, and liquid compositions such as solution, suspension and the like.

When Compound (I) is administered non-orally, it may be used also as injection, drop injection, suppository and the like.

Though the amount of active ingredient in the composition varies with composition form, it is usually in the range of 0.1 to 70% (W/W) and preferably 1 to 50% (W/W) in the case of solid compositions and in the range of 0.01 to 30% (W/V) and preferably 0.05 to 20% (W/V) in liquid compositions.

The compositions suitable for the above-mentioned administering methods are produced according to the conventional processes.

The dose of the composition of the present invention for use in the treatment of heart failure of mammals varies depending on the symptom, age, body weight, etc. of the patient. Usually, however, it is administered in an amount of 0.002 to 60 mg (as expressed by the weight of active ingredient) and preferably about 0.2 to 20 mg per kg of the body weight.

The composition of the present invention for use in the treatment of heart failue of mammals is quite low in toxicity, so that it can remarkably improve the state of acute or chronic heart failure without any side reactions. Thus, the present invention is quite valuable from the industrial point of view.

Next, the present invention will be illustrated more concretely with reference to the following examples and test examples.

EXAMPLE 1

(Injection)

Ninety grams of sterilized sodium salt of $N^6$-heptyl-adenosine-3',5'-cyclic phosphate was dissolved into injection distilled water and the total volume was adjusted to 3.0 liters. Thirty milliliter portions of the resulting solution were aseptically sealed into ampoules, and used as injections.

EXAMPLE 2

(Oral tablet)

| | | |
|---|---|---|
| (1) | Sodium $N^6$—Heptyl-adenosine-3',5'-cyclic phosphate | 250 g |
| (2) | Mannitol | 200 g |
| (3) | Potato starch | 47 g |
| (4) | Magnesium stearate | 3 g |

Ingredients (1) and (2) were mixed together, to which was added (3) in the form of a 10% starch paste. The mixture was formed into granule, passed through a No. 60 mesh sieve (B. S.), dried, and then again fractionated by means of No. 16 mesh sieve (B. S.). The granule thus obtained was mixed with (4) and formed into tablet by means of a tablet machine. The tablet thus obtained had a diameter of 10 mm and a weight of 500 mg/one tablet.

EXAMPLE 3

(Suppository)

Twenty five grams of sterilized $N^6$-heptyladenosine-3',5'-cyclic phosphate was added to 975 g of O.D.O. (triglyceride of middle chain fatty acid, manufactured by Nisshin Seiyu K.K.) and thoroughly homogenized. Then, the mixture was filled into a gelatin soft capsule film. Thus, a suppository capsule containing 125 mg of active ingredient per one capsule was obtained.

TEST EXAMPLE 1

Test animal: guinea-pigs

Method of Experiment: extirpated guinea pig papillary muscle preparation.

Male albino guinea pigs having body weights of 300 to 500 g were stunned by a blow on the head. The hearts were quickly extirpated and the papillary muscles of the right ventricle were dissected out in cold bathing solution (2° to 4° C.), and were suspended in a 10 ml organ bath for recording isometric contractions. The bathing solution was the Krebs-Henseleit solution (32°±0.5° C.) and was continuously bubbled with a mixed gas composed of 95% $O_2$ and 5% $CO_2$. The papillary muscle preparation were stimulated by square wave pulses of 1 msec duration at the frequency of 1 Hz and at voltages of 20% above the threshold supplied by a square-wave pulse stimulator via a pair of the silver plate electrodes in which the preparations were placed.

The isometric contraction was measured by a force-displacement transducer connected to a carrier-amplifier.

The test solution was prepared by dissolving the sodium salt into distilled water or dissolving the free acid into Krebs-Henseleit solution.

In Table 1 are shown the observed contractive forces of the papillary muscles in experiments using $10^{-3}$M solution of $N^6$-substituted-C-AMP and salts thereof. The results are shown as relative values (%), taking the result given by a reaction using $10^{-7}$M Isoproterenol (positive control) as 100%.

TABLE 1

| | Increase in contractive force (%) |
|---|---|
| $N^6$—Isobutyl-C—AMP | 24.0 |
| $N^6$—Butyl-C—AMP | 71.0 |
| $N^6$—Pentyl-C—AMP | 98.0 |
| $N^6$—Heptyl-C—AMP | 94.1 |
| $N^6$—Nonyl-C—AMP Na | 49.5 |
| $N^6$—Benzyl-C—AMP Na | 91.7 |
| $N^6$—Furfuryl-C—AMP Na | 93.2 |

Table 1 demonstrates the very excellent therapeutic effect of the composition of the present invention on heart failure of mammals.

TEST EXAMPLE 2

Test animal: Crossbred adult dogs (female and male)

Method of Experiment: cardiotonic activity on heart-lung preparation.

Using female and male crossbred dogs having body weights of 9 to 10 kg anesthetized with Pentobarbital, heart-lung preparations were prepared in the usual way, on which systemic output, right atrium pressure and heart rate were measured.

After inducing a state of acute heart failure by administering 100 mg of Pentobarbital into the blood reservoir in the circulatory circuit, 10 mg or 30 mg of sodium salt of $N^6$-heptyl-adenosine-3',5'-cyclic phosphate dissolved in 1 ml of distilled water was administered, and its cardiotonic activity was measured by taking systemic output and right atrium pressure as indices. The results were as shown in Table 2. Regarding the control (no administration group), the results express the values after administration of Pentobarbital.

TABLE 2

| Dose | Systemic output (ml/min./ 100 g heart) [Increase] | | Right atrium pressure (mm $H_2O$) [Decrease] | | Heart rate (beats/min.) [Change] | |
|---|---|---|---|---|---|---|
| Control | 259 | | 109 | | 110 | |
| 10 mg | 409 | [150] | 96.9 | [12.1] | 112 | [2] |
| 30 mg | 610 | [351] | 68.3 | [40.7] | 120 | [10] |

Increase in systemic output = Systemic output in administration group − Systemic output in non-administration group.
Decrease in right atrium pressure = Right atrium pressure in non-administration group − Right atrium pressure in administration group.
Change in Heart rate = Heart rate in administration group − Heart rate in non-administration group.

The results shown in Table 2 demonstrate that the acute heart failure state induced by Pentobarbital is remarkably improved by administration of $N^6$-heptyl-C-AMP, with an increase in systemic output and a decrease in the right atrium pressure.

TEST EXAMPLE 3

(Acute toxicity)

Test animal: female ICR-CRJ: CD-1 mice, 5 weeks old, body weight 29 to 32 g

Method of experiment:

$N^6$-substituted-C-AMP dissolved in dimethyl sulfoxide was intraperitoneally administered to 5-weeks old ICR-CRJ: CD-1 mice (female, body weight 29–32 g) at a dose rate of 0.05 ml per 30 g body weight, and thereafter the animals were observed for 7 days. The results were as shown in Table 3.

$LD_{50}$ was calculated according to the Richfield-Wilcockson method (Pharmacological Tests, p 200–205, Nanzando, 1967).

TABLE 3

|  | $LD_{50}$ (mg/kg) |
|---|---|
| $N^6$—Butyl-C—AMP | 350 |
| $N^6$—Heptyl-C—AMP | 174 |
| $N^6$—Nonyl-C—AMP Na | 150 |
| $N^6$—Benzyl-C—AMP Na | 383 |
| $N^6$—Furfuryl-C—AMP Na | 483 |

What is claimed is:

1. A method for the treatment of heart failure of a mammal which comprises administering, per kilogram of body weight of said mammal, 0.002 to 60 mg per day of an $N^6$-substituted-adenosine-3',5'-cyclic phosphate represented by the following general formula or a physiologically acceptable salt thereof:

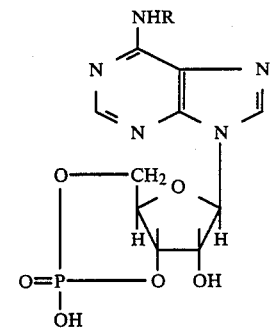

wherein R represents an alkyl group selected from the group consisting of ethyl, propyl, isopropyl, butyl, isobutyl, pentyl, isopentyl, hexyl, isohexyl, cyclohexyl, heptyl, isoheptyl, octyl, isooctyl, nonyl, isononyl, decyl, undecyl, dodecyl, tridecyl, and tetradecyl group, or an aralkyl group selected from the group consisting of furfuryl, benzyl, phenethyl, chlorobenzyl, hydroxybenzyl, methylbenzyl and methoxybenzyl.

2. A method according to claim 1 wherein said $N^6$-substituted-adenosine-3',5'-cyclic phosphate is administered in a composition containing a pharmaceutically acceptable carrier.

3. A method according to claim 1, wherein said physiologically acceptable salt is an alkali metal salt, an ammonium salt or an organic ammonium salt.

4. A method according to claim 1, wherein said physiologically acceptable salt is a potassium salt or a sodium salt.

5. A method according to claim 2, wherein the composition has a form of tablet, pill, powder, capsule or granule.

6. A method according to claim 5, wherein the content of $N^6$-substituted-adenosine-3',5'-cyclic phosphate is 0.1 to 70% (W/W) in the composition.

7. A method according to claim 2, wherein the composition has a form of a solution or a suspension.

8. A method according to claim 7, wherein the content of $N^6$-substituted-adenosine-3',5'-cyclic phosphate is 0.01 to 30% (W/V) in the composition.

9. A method according to claim 2, wherein the pharmaceutically acceptable carrier is at least one member selected from the group consisting of binders, excipients, lubricants, disintegrators, wetting agents, dissolving agents and dispersants.

* * * * *